United States Patent [19]

Ivanov

[11] Patent Number: 5,696,586
[45] Date of Patent: Dec. 9, 1997

[54] OPTICAL CORRELATION GAS ANALYZER

[75] Inventor: Evgeniy Vladimirovich Ivanov, Saskatoon, Canada

[73] Assignee: Sci-Tec Instruments Inc., Canada

[21] Appl. No.: 618,904

[22] Filed: Mar. 20, 1996

[30] Foreign Application Priority Data

Mar. 21, 1995 [RU] Russian Federation .............. 95103979

[51] Int. Cl.$^6$ ....................................................... G01J 4/00
[52] U.S. Cl. ........................................... 356/364; 356/365
[58] Field of Search ..................................... 356/364, 365, 356/366, 367, 368, 51, 346, 351; 350/403, 404; 359/885

[56] References Cited

U.S. PATENT DOCUMENTS

| | | | |
|---|---|---|---|
| 4,320,973 | 3/1982 | Fortunato et al. | 356/346 |
| 4,626,100 | 12/1986 | Johnson | 356/152 |
| 4,822,169 | 4/1989 | Distl et al. | 356/364 |
| 5,128,797 | 7/1992 | Sachse et al. | 359/246 |
| 5,155,552 | 10/1992 | Fortunato et al. | 356/346 |
| 5,218,422 | 6/1993 | Zoechbauer | 356/352 |
| 5,483,387 | 1/1996 | Bauhahn et al. | 359/885 |

FOREIGN PATENT DOCUMENTS

| | | |
|---|---|---|
| 396319 | 11/1990 | European Pat. Off. . |
| 396320 | 11/1990 | European Pat. Off. . |
| 2420754 | 10/1979 | France . |
| 2581190 | 4/1985 | France . |
| 1293535 | 2/1987 | U.S.S.R. . |
| 1156467 | 9/1997 | U.S.S.R. . |
| 2174198 | 10/1986 | United Kingdom . |

OTHER PUBLICATIONS

"Mathematical Handbook for Scientists and Engineers" Korn et al McGraw-Hill Book COmpany, Moscow, 1984; pp. 134–144 & 900–905.

"Numerical Recipes in C" Press et al; Cambridge University Press Fourier Transform of Discretely Sampled Data; 1988; pp. 402–405.

"The Fourier Transform Spectrometer"; Meaburn; Detection and Spectrometry of Faint Light, Dordrecht/Boston, 1976. Chapter 9 pp. 203–221.

"Zaidel A.N., Ostrovskaya G.V, Ostrovskiy Y.I Technics and Practice of Spectroscopy" Moscow; 1976 pp. 246–251.

*Primary Examiner*—Frank G. Font
*Assistant Examiner*—Michael P. Stafira
*Attorney, Agent, or Firm*—Hayes, Soloway, Hennessey, Grossman & Hage, P.C.

[57] ABSTRACT

An optical gas analyzer includes optical, mechanical and electronic systems. The optical system includes a collimator, a light filter, a modulated interference polarization filter (IPF), and a photo detector. The modulated IPF has two polarizers, crossed or parallel to each other, with an optical modulator and a birefringent plate mounted between them. The birefringent plate has a variable thickness which is mechanically driven and controlled by the electronic system via the electro-mechanical driver. The photo detector has its output connected to the electronic system and is placed after IPF. The gas analyzer has the advantage of allowing the minimum detectable limit of the concentration of measured gas to be decreased by greatly reducing the influence of parasitic modulation. Parasitic modulation is induced by the optical modulator into the optical and electronic units of the gas analyzer and affects the output signal. However, synchronous modulation of the modulated IPF cancels the parasitic effect in the final output, based upon the difference of two such measurements.

3 Claims, 1 Drawing Sheet

OPTICAL CORRELATION GAS ANALYZER

FIELD OF THE INVENTION

The present invention relates to atmospheric pollution measuring and environmental monitoring and is particularly concerned with optical correlation gas analyzers.

BACKGROUND OF THE INVENTION

In the prior art there are optical gas analyzers that use the correlation spectroscopy method to measure the gas concentration present in the path between the light source and the gas analyzer. As described in: Zaidel A. N., Ostrovskaya G. V, Ostrovskiy Y. I., Technics and Practice of Spectroscopy, Moscow, "Science", 1976, a modulated interference polarization filter (IPF), is used as the discriminatory element. The IPF consists of two polarizers, crossed or parallel to each other, with a birefringent element and modulator mounted between them. The birefringent element is in the form of a plate made of a birefringent crystal with the optical axis perpendicular to the optical axis of the gas analyzer and at 45° with respect to the polarization axes. The modulator induces an alternating light path difference, $\delta$, in addition to the light path difference $\Delta$, that occurs between the ordinary and extraordinary rays as a result of the birefringent plate. In this case the absorption spectrum of the measured gas is correlated with the spectral transmission function of the IPF:

$$T(\lambda) = \cos^2\left[\frac{\pi \cdot (\Delta + \delta)}{\lambda}\right] = \frac{1}{2} \cdot \left(1 + \cos\left[\frac{2\pi \cdot (\Delta + \delta)}{\lambda}\right]\right)$$

where $T(\lambda)$ is the spectral transmission function of the IPF, $\lambda$ is the wavelength, $\Delta = L(n_o - n_e)$ is the light path difference in the birefringent plate, L is the thickness of the birefringent plate, and no and ne are the ordinary and extraordinary indices of refraction of the birefringent plate. The characteristic structure of the molecular absorption spectra of the target gas is periodic, as is the transmission function $T(\lambda)$. The length of the birefringent plate is selected such that the light path difference, $\Delta$, will produce a spacing in the transmission function $T(\lambda)$, with the same periodic frequency as the absorbing gas. When the modulator induces a light path difference, $\delta$ the modulation intensity of the light incident on the photo detector occurs in the presence of the measured gas. This modulation measured by the electronic unit is related to the optical depth (product of the gas concentration and the light path length) of the measured gas and can be approximated by a power law:

$$M = c_1 \cdot OD^{c_2}$$

where M is the modulation amplitude, $c_1$ and $c_2$ are constants, and OD is the optical depth of the gas.

Some examples of instruments, as described above, are gas analyzers that use an optical modulator made of a photoelastic material plate connected to a piezoelectric converter as taught by: Auth. Cert. of Russia SU N 1293585, G 01 N 21/61, Publ. 02.28.87; and France Patent No. 2581190, G 01 N 21/45, Publ. 1986; or solid crystal electro-optical plate, as taught by: Auth. Cert. of Russia SU N 1156467, G 01 N 21/41, Publ. 09.15.87.

A crystal quartz plate can be used as the birefringent element as in French Patent No. 2581190, or a pair of crystal quartz wedges can be used for the purpose of accurately adjusting the light path difference, $\Delta$, and allowing for the possibility of making multi-gas measurements as in French Patent No. 2420754, G 01 N 21/46,31/12, G 05 D 11/00, Publ. 1979. One of the drawbacks of these devices may be the presence of parasitic modulation (a false signal induced by the modulator into the optical unit and by the modulator driver into the electronic unit). Parasitic modulation results in a shift of the instrument zero that is independent of the presence of the measured gas.

The prototype optical gas analyzer taught in Russian Authors Certificate SU No. 1156467, which consists of the two polarizers, crossed or parallel to each other, with the following elements between them: a birefringent plate with its optical axis perpendicular to optical axis of the gas analyzer, and a modulator in the form of a plate with its optical axis parallel to the optical axis of the gas analyzer. The modulator is made from a birefringent crystal, with at least one of its electro-optical coefficients $K_{41}$, $K_{52}$, $K_{63}$ being non-zero, and sandwiched between two electrodes connected to an AC generator. A signal from photomultiplier tube (PMT) is input to a narrow-band amplifier, a synchro-detector and an indicator. The PMT power supply is included in a feedback circuit with the aid of a PMT automatic gain control (AGC). The purpose of the AGC is to maintain a constant component of the PMT current at a pre-determined level regardless of the light intensity. One of the drawbacks of this prototype is the presence of parasitic modulation, induced by the modulator into the optical unit. The parasitic modulation depends upon the angle between the incoming light beam and the optical axis of the instrument, as well as the light intensity distribution across the entrance pupil aperture. Furthermore, parasitic modulation is induced by the modulator driver into electronic unit, in particular the AGC circuit, and therefore depends on the light intensity. Any change in these factors affecting parasitic modulation that occurs during the measurement process, leads to a shift in the instrument zero and restricts the minimum detectable limit of the measured gas concentration.

SUMMARY OF THE INVENTION

An object of the present invention is to provide an improved optical correlation gas analyzer.

The objective of the present invention is achieved by reducing the minimum detectable limit of the instrument by reducing the influences of parasitic modulation on the output signal.

In accordance with an aspect of the present invention there is provided an optical gas analyzer comprising a collimator, a light filter, a modulated interference polarization filter (IPF), and a photo detector, the collimator, the light filter, the IPF, and photo detector in series, and an electronic unit connected to the photo detector, wherein the modulated IPF includes two polarizers, crossed or parallel to each other, a birefringent element, and an optical modulator placed between the polarizers, and wherein the birefringent element comprises a variable thickness plate, the thickness of the plate being mechanically selected and controlled by the electronic unit by means of the electro-mechanical driver, whereby the modulation depth of the radiation incident on the photo detector is first measured at a plate thickness selected such that the periodicity of the interference polarization filter transmission function substantially matches the periodicity of the gas absorption spectrum, and the intensity difference induced by the electro-optical modulator is at a local maximum, and is then measured at a second plate thickness with a corresponding periodic transmission function phase of the IPF displaced by substantially 180 degrees, so that a modulation amplitude is also at a local extrema, but is of opposite sign, and whereby these measurement results being then subtracted in the electronic unit to derive an indication of the gas concentration.

In a embodiment of the present invention, the birefringent plate comprises two birefringent wedges with the optical axes oriented perpendicular to the optical axis of the analyzer, and wherein the electronic unit includes electro-mechanical driver, the two wedges arranged for relative movement therebetween responsive to the driver as controlled by the electronic unit.

According to the present invention the objective of the invention is achieved by using a birefringent plate with an adjustable thickness instead of a birefringent plate of constant thickness. The adjustable thickness is mechanically selected by an electro-mechanical driver that is controlled by the electronic unit.

According to another aspect of the present invention there is provided an optical gas analyzer comprising an optical system including a modulated interference polarization filter and an optical modulator, a mechanical system coupled to modulated interference filter, and an electronic system coupled to the optical modulator and the modulated interference filter, whereby a modulation depth of radiation is first measured with the interference polarization filter in a first condition such that the periodicity of the interference polarization filter transmission function substantially matches the periodicity of the gas absorption spectrum, and the intensity difference induced by the optical modulator is at a local maximum, and a second modulation depth of radiation is then measured with the interference polarization filter in a second condition such that a corresponding periodic transmission function phase of the IPF is displaced by substantially 180 degrees, so that a modulation amplitude is also at a local extrema, but is of opposite sign, and whereby these measurement results are then subtracted in the electronic unit to derive an indication of the gas concentration.

In accordance with a further aspect of the present invention there is provided an optical gas analyzer comprising an optical system, the optical system includes a collimator, a light filter, a modulated interference polarization filter (IPF), and a photo detector, a mechanical system including an electro-mechanical driver, and an electronic system; the modulated IPF having two polarizers, crossed or parallel to each other, with an optical modulator and a birefringent plate mounted between them, the birefringent plate having a variable thickness which is mechanically driven and controlled by the electronic system via the electro-mechanical driver, whereby the optical gas analyzer allows the minimum detectable limit of concentration of a measured target gas to be decreased by greatly reducing the influence of parasitic modulation induced by the optical modulator into the optical and electronic units of the gas analyzer and affects the output signal by synchronous modulation of the modulated IPF thereby cancelling the parasitic effect in the final output, based upon the difference of two such measurements.

An advantage of the present invention is allowing the minimum detectable limit of concentration of a measured target gas to be decreased by greatly reducing the influence of parasitic modulation induced by the optical modulator into the optical and electronic units of the gas analyzer and affects the output signal by synchronous modulation of the modulated IPF thereby cancelling the parasitic effect in the final output.

BRIEF DESCRIPTION OF DRAWINGS

The present invention will be further understood from the following description with references to the drawings in which:

The figure illustrates, in a block diagram, a gas analyzer in accordance with an embodiment of the present invention.

DETAILED DESCRIPTION

Figure 1:
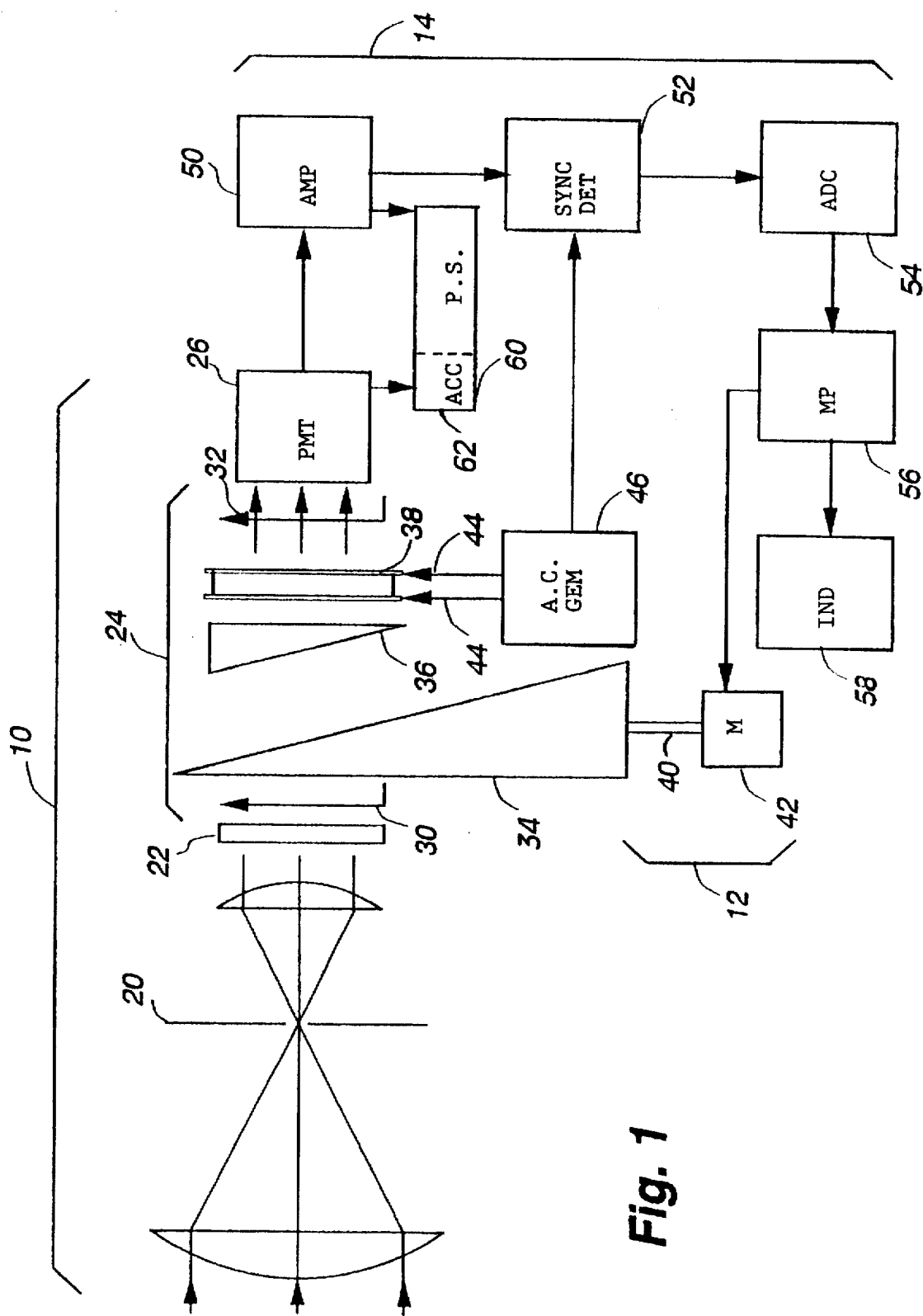

Referring to the figure, there is illustrated a gas analyzer in accordance with an embodiment of the present invention. The gas analyzer comprises optical 10, mechanical 12, and electronic 14 systems that are all interdependent. The optical system 12 includes a collimator 20, a light filter 22, an interference polarizing filter (IPF) 24, and a photomultiplier tube (PMT) detector 26. The IPF 24 includes crossed polarizers 30 and 32, a moving wedge 34 and a fixed wedge 36, and an electro-optical modulator 38. The wedges 34 and 36 are made of crystal quartz with their axes perpendicular to the optical axis of the analyzer.

The mechanical system 12 includes a micrometer screw 40 and a stepping motor 42. The moving wedge 34 is kinematically connected to the micrometer screw 40 and driven by the stepping motor 42.

The electro-optical modulator 38 is a DKDP crystal plate with its optical axis oriented parallel to the optical axis of the analyzer. The modulator 38 is sandwiched between two electrodes 44 connected to an AC generator 46. The PMT detector 26 is placed after the IPF 24.

The electronic system 14 includes a narrow band amplifier 50, a synchro-detector 52, an analog to digital converter 54, and a microprocessor 56. The electronic system controls the stepping motor 42, an indicator 58, and a PMT power supply 60 with an AGC circuit 62.

In operation, the gas analyzer functions in the following manner. The light filter 22 transmits the working spectral region that corresponds to the absorption spectrum of the measured gas. The modulated IPF 24 produces a transmission function with a periodicity similar to the absorption signature of the measured gas, but with a modulated phase difference. This results in an intensity modulation on the detector in the presence of the gas. The electronic system 14 measures the modulation depth of the light incident on the PMT detector 26, synchronous with the IPF modulation. The variable thickness of the birefringent plate, formed by the two wedges 34 and 36, determines the maxima positions of the IPF transmission function. The variable thickness of the birefringent plate is controlled by translating the moving wedge 34 by the micrometer screw 40, which is connected to the stepping motor 42, and controlled by the microprocessor 56. The measurement cycle is organized so that the moving wedge 34 is first translated to a position 1 that corresponds to a maxima of the modulation amplitude produced by the interaction of the transmission function $T(\lambda)$ and the absorption spectrum of the measured gas. The microprocessor 56 then measures and stores the value of the modulation depth M1. The moving wedge 34 is then translated to a position 2 which corresponds to another maxima of the modulation amplitude, 180 degrees out of phase with the first measurement. The microprocessor 56 then measures and stores the value of the modulation depth M2. The microprocessor 56 then calculates the log of the difference (M1−M2), multiplies the result by a calibration slope and intercept, and displays the antilog of this value on the indicator 58. The measurement cycle is then repeated.

The plate thickness $L_1$, is selected such that the periodicity of the IPF transmission function matches the periodicity of the gas absorption spectrum, and that the intensity difference induced by the electro-optical modulator, $M_1$, is at a local maximum. A second plate thickness $L_2$ displaces the periodic transmission function phase of the IPF 180 degrees.

This results in a modulation amplitude which is also at a local extrema, but is of opposite sign. The measured results of $M_1$ and $M_2$ are then subtracted in the electronic unit. The parasitic modulation induced by the modulator, P, does not depend on the plate thickness, L (i.e. $P_1=P_2$). Because the modulation signature from the gas, G, changes sign, and the parasitic modulation is constant and positive we find:

$$M_1=G_1+P_1, M_2=G_2+P_2, M_1-M_2=G_1+G_2.$$

Hence, the influence of parasitic modulation on the measured result is eliminated by taking the difference between $M_1$ and $M_2$.

Although the mechanical adjustment of the birefringent plate thickness complicates the arrangement of the gas analyzer, it simultaneously decreases the minimum detectable limit of the measured gas concentration by more than a factor of ten. This decrease in the minimum detectable limit is achieved by eliminating the influence of parasitic modulation on the optical and electronic units. In addition, it allows for sequential measurements of a number of gases by adjusting the thickness of the birefringent plate and, if necessary, switching the light filter.

Numerous modifications, variations, and adaptaions may be made to the particular embodiments of the invention described above without departing from the scope of the invention, which is defined in the claims.

What is claimed is:

1. A gas analyzer comprises:

an optical system, the optical system includes a collimator, a light filter, a modulated interference polarization filter (IPF), and a photo detector;

a mechanical system including an electro-mechanical driver; and an electronic system;

the modulated IPF having two polarizers with an optical modulator and a birefringent plate mounted between them;

the birefringent plate having two birefringent wedges with the optical axes oriented perpendicular to the optical axis of the analyzer which are arranged for relative movement therebetween responsive to the driver as controlled by the electronic unit between first and second positions, the first position corresponding to a first maximum output of the photo detector and the second position corresponding to a second maximum output of the photo detector to effect two measurements; wherein the optical gas analyzer allows the minimum detectable limit of concentration of a measured target gas to be decreased by greatly reducing the influence of parasitic modulation induced by the optical modulator into the optical and electronic units of the gas analyzer and affecting the output signal by synchronous modulation of the modulated IPF thereby canceling the parasitic effect in the final output, based upon the difference of the two measurements.

2. A gas analyzer as claimed in claim 1 wherein the two polarizers are oriented with their polarization axes parallel.

3. A gas analyzer as claimed in claim 1 wherein the two polarizers are oriented with their polarization axes crossed.

* * * * *